United States Patent [19]
Rohr

[11] Patent Number: 5,431,657
[45] Date of Patent: Jul. 11, 1995

[54] INSTRUMENT FOR INSTALLING AN ACETABULAR CUP ASSEMBLY

[75] Inventor: William Rohr, Warsaw, Ind.

[73] Assignee: Zimmer, Inc., Warsaw, Ind.

[21] Appl. No.: 247,813

[22] Filed: May 23, 1994

[51] Int. Cl.⁶ .................. A61F 2/46; A61B 17/88; A61B 17/92
[52] U.S. Cl. ............................... 606/91; 606/99
[58] Field of Search ................ 606/99, 91; 623/22

[56] References Cited

U.S. PATENT DOCUMENTS

| | | |
|---|---|---|
| 4,305,394 | 12/1981 | Bertuch, Jr. |
| 4,632,111 | 12/1986 | Roche . |
| 4,662,891 | 5/1987 | Noiles ................ 623/22 |
| 4,716,894 | 1/1988 | Lazzeri et al. . |
| 4,795,469 | 1/1989 | Oh ...................... 623/22 |
| 4,802,468 | 2/1989 | Powlan . |
| 4,878,918 | 11/1989 | Tari et al. ........... 623/22 |
| 4,987,904 | 1/1991 | Wilson . |
| 4,994,064 | 2/1991 | Aboczsky ........... 606/91 |
| 5,037,424 | 8/1991 | Aboczsky ........... 606/91 |
| 5,061,270 | 10/1991 | Aboczsky ........... 606/91 |
| 5,098,437 | 3/1992 | Kashuba et al. ... 606/89 |
| 5,116,339 | 5/1992 | Glock ................. 606/91 |
| 5,156,626 | 10/1992 | Broderick et al. . 623/22 |
| 5,169,399 | 12/1992 | Ryland et al. ..... 606/91 |
| 5,171,243 | 12/1992 | Kashuba et al. ... 606/86 |
| 5,171,312 | 12/1992 | Salyer ................ 606/81 |

FOREIGN PATENT DOCUMENTS 0147339 7/1985 European Pat. Off. .
0535973 4/1993 European Pat. Off. ........ 606/61

Primary Examiner—Tamara L. Graysay
Assistant Examiner—Scott B. Markow
Attorney, Agent, or Firm—Todd A. Dawson

[57] ABSTRACT

An instrument 2 used to install both the outer shell 40 and bearing liner 50 of a conventional acetabular cup assembly 4. Instrument 2 includes an impactor 30 and a reversible cup or head component 10, which is adapted for driving shell 40 into the acetabulum and for seating bearing liner 50 into the shell. Head component 10 has a rounded semi-spherical surface 12 on one end and a substantially flat surface 14 on the opposite end. Impactor 30 includes a longitudinal extension 36 which can be inserted into a bore 20 in head component 10 from either direction to secure the head component to the impactor. When instrument 2 is used to seat shell 40 into the acetabulum, head component 10 is fitted to impactor 30 with semi-spherical surface 12 facing outward for abutment against inner surface 44 of shell 40. Shell 40 is connected to the distal end 39 of extension 36, which protrudes from semi-spherical surface 12 of head component 10. When instrument 2 is used to seat bearing liner 50 into shell 40, head component 10 is connected to impactor 30 with flat surface 14 facing outward for abutment against bearing liner 50.

6 Claims, 2 Drawing Sheets

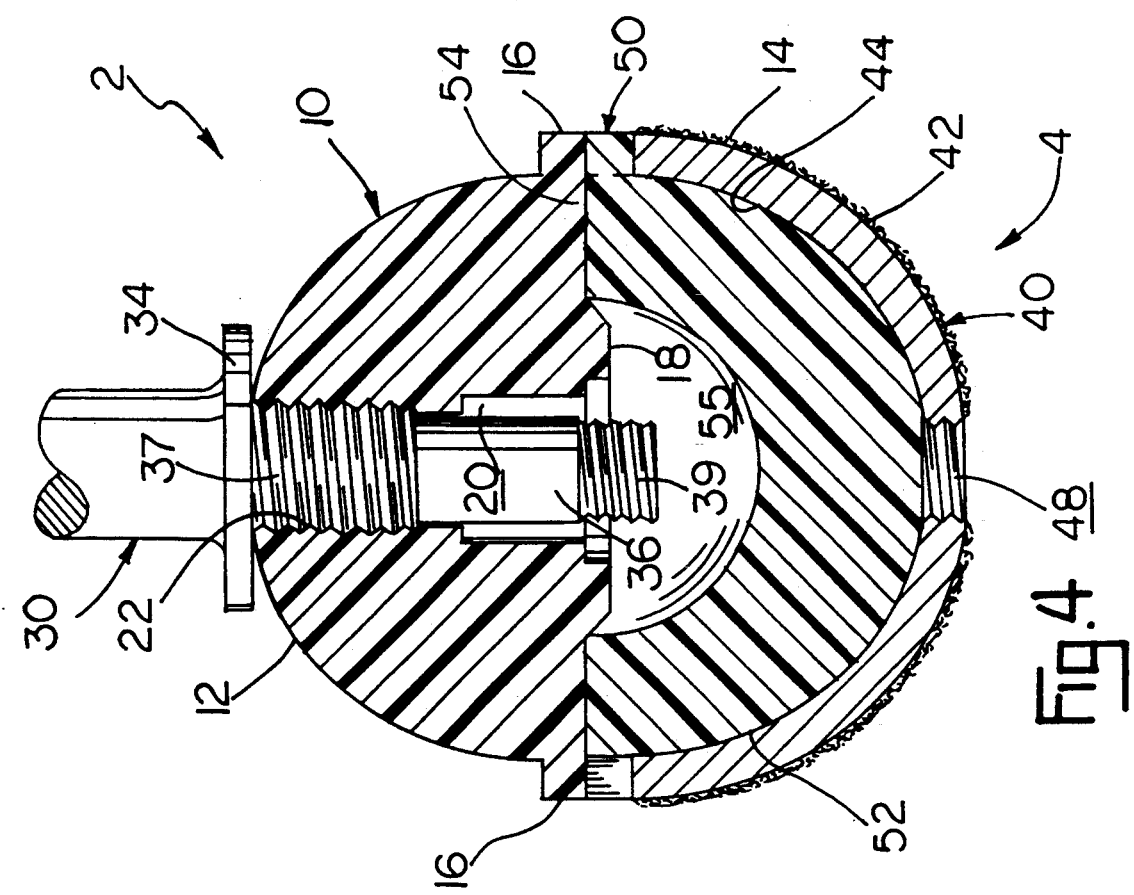
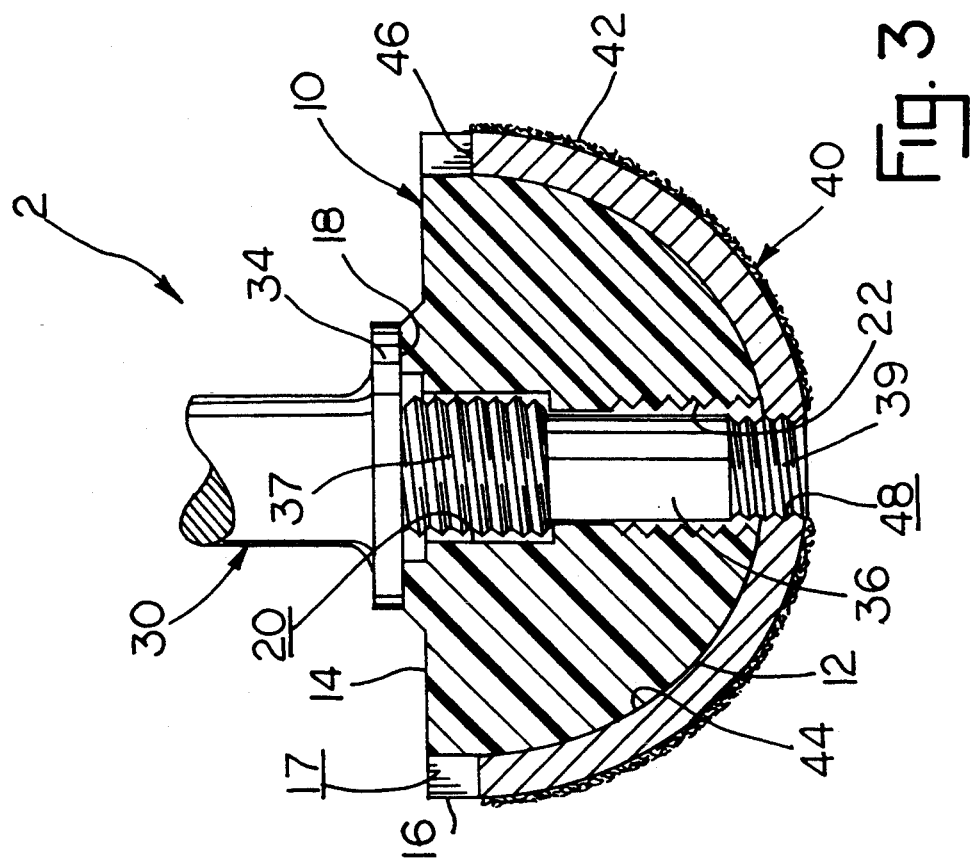

INSTRUMENT FOR INSTALLING AN ACETABULAR CUP ASSEMBLY

This invention relates to an instrument for installing an acetabular cup implant, and particularly an instrument for installing both the outer cup or shell and inner bearing liner of the acetabular cup assembly.

BACKGROUND OF INVENTION

Instruments for positioning and installing acetabular cup assemblies into hip bones are well known in the field of orthopedic medicine. Conventional prosthetic cup assemblies include a semi-spherical outer cup or shell and a polymer bearing liner. The shell is positioned and seated into the acetabulum of a patient by an impactor which is used to seat the shell into the prepared acetabulum. Typically, the shell is temporarily secured to the distal end of an impactor. Mounting the shell to the impactor allows the shell to be easily aligned and securely positioned as the impactor is used to seat the shell into the acetabulum. Once the shell is securely seated in the acetabulum, the impactor is disconnected and the liner is fitted to the shell. While the liner generally snaps into the shell, a separate instrument occasionally may be required to insert the bearing liner into the shell. The additional instrument used to seat the bearing liner adds to the total instrument count in the surgical procedure.

SUMMARY OF INVENTION

The instrument of this invention is used to install both the outer shell and bearing liner of a conventional acetabular cup assembly. The instrument includes an impactor and a reversible cup or head component, which is adapted for seating the shell into the acetabulum and for inserting the bearing liner into the shell. The head component can be fitted to the distal end of the impactor in one position for seating the shell and in another position for seating the liner. The head component has a semi-spherical surface on one end for engagement against the inner surface of the shell and a substantially flat surface on the opposite end for abutment against the liner. The impactor includes a longitudinal extension which can be inserted into a bore in the head component from either direction to fit the head component to the impactor. The extension has a threaded proximal end for connecting the head component to the impactor and a threaded distal end for connecting the instrument to the shell.

In use, the instrument is seated using an impaction instrument to install the cup assembly. When the instrument is used to seat the shell into the acetabulum, the head component is fitted about the extension with the semi-spherical surface facing outward for abutment against the inner surface of the shell. The shell is connected to the threaded distal end of the extension, which protrudes from the semi-spherical surface of the head component. The head component is secured between the shell and the impactor with the inner surface of the shell seated against the semi-spherical surface of the head component. Once the shell is driven into the acetabulum, the instrument is disconnected from the shell. When the instrument is used to seat the bearing liner into the shell, the head component is connected to the impactor with the flat surface facing outward for abutment against the bearing liner. With the flat surface of the head component abutted against the bearing liner, the instrument is impacted to seat the bearing liner within the shell without damaging the liner.

Accordingly, an advantage of this invention is to provide an instrument which reduces the number of instruments needed to install an acetabular cup assembly, which includes an outer shell and a bearing liner.

Another advantage of this invention is to provide for an instrument used to install an acetabular cup assembly which can be used to seat both the outer shell and bearing liner.

Another advantage of this invention is to provide for an instrument used to install an acetabular cup assembly, which includes an impactor and a reversible head component that is adapted for abutment against the shell on one side and the bearing liner on the opposite side.

Other advantages will become apparent upon a reading of the following description.

BRIEF DESCRIPTION OF THE DRAWINGS

A preferred embodiment of the invention has been depicted for illustrative purposes only wherein:

FIG. 3 is a sectional view of the instrument showing the head component connected to the impactor for seating the acetabular shell to the acetabulum; and FIG. 4 is a sectional view of the instrument showing the head component connected to the impactor for fitting the shell liner within the acetabular shell.

DESCRIPTION OF THE PREFERRED EMBODIMENT

The preferred embodiment herein described is not intended to be exhaustive or to limit the invention to the precise form disclosed. It is chosen and described to explain the principles of the invention and its application and practical use to enable others skilled in the art to utilize its teachings.

Figure 2:
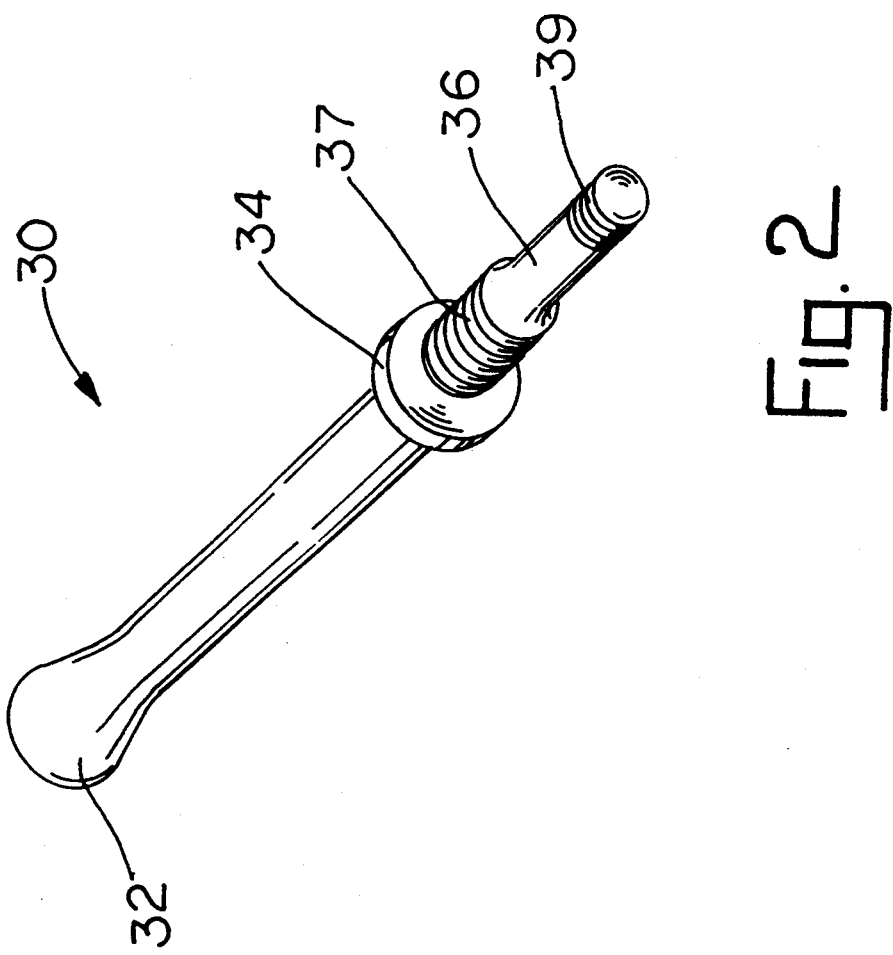
FIG. 2 is a perspective view of the impactor of the instrument of this invention.
Figure 1:
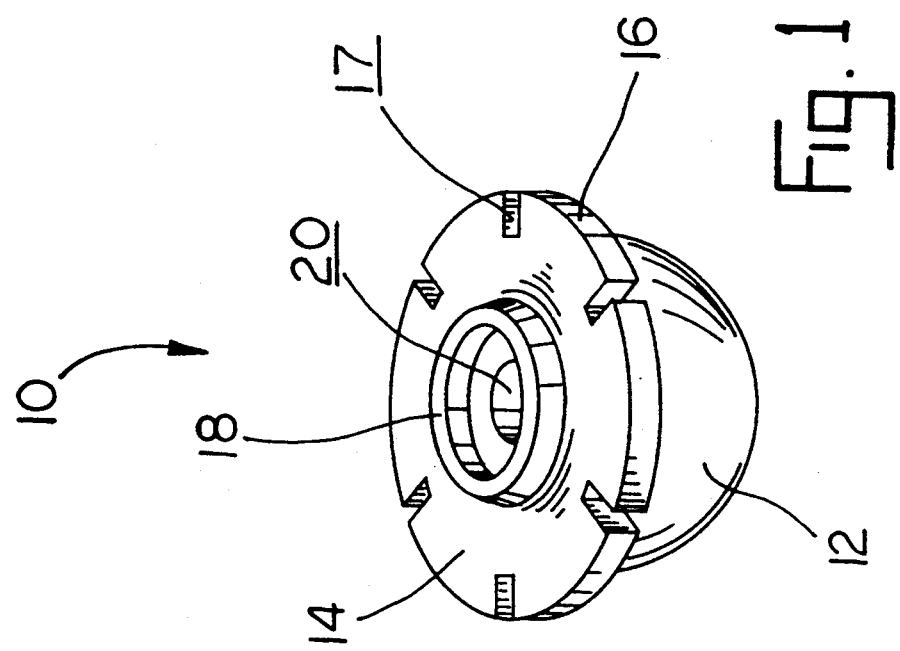
FIG. 1 is a perspective view of the head component of the instrument of this invention.

FIGS. 1 and 2 show the reversible cup or head component 10 and the impactor 30 of the installation instrument 2 of this invention. The instrument is designed to be used with a conventional acetabular cup assembly 4 (shown in FIGS. 3 and 4). The individual components of the instrument can be fabricated from stainless steel, titanium, or other suitable material.

As shown in FIG. 1, head component 10 has a rounded semi-spherical surface 12 forming the shell engaging end and a substantially flat circular surface 14 forming a liner engaging end. Head component 10 includes a radially projecting side flange 16. Six notches 17 are formed along the perimeter of side flange 16. Head component 10 has a longitudinal center bore 20 extending between the apex of rounded surface 12 and the center of flat surface 14. As shown in FIGS. 3 and 4, the diameter of bore 20 at the liner engaging end is greater than the diameter of bore 20 at the shell engaging end. As shown in FIGS. 3 and 4, bore 20 has an internally threaded portion 22 formed at the shell engaging end. An annular rim 18 protrudes from flat surface 14 concentrically about bore 20.

Impactor 30 includes a contact head 32 formed at its proximal end and an annular flange 34 formed at its distal end. As is commonly known in the field, a mallet or other striking instrument (not shown) is used to strike contact head 32 to drive the acetabular cup assembly into the acetabulum. Impactor 30 also includes an integral extension 36 extending axially from the distal end of impactor 30. Extension 36 has an externally threaded proximal end 37 directly adjacent flange 34, and an externally threaded distal end 39. As shown in the figures, the outer diameter of threaded distal end 39 is smaller than the outer diameter of threaded proximal end 37. As shown in the FIGS. 3 and 4, head component 10 can be connected to impactor 30 in two separate orientations or impacting positions for use in setting either shell 40 or liner 50. Extension 36 can be inserted into bore 20 from either direction.

As shown in FIGS. 3 and 4, cup assembly 4 includes an outer cup or shell 40 and an inner bearing component or liner 50. Shell 40 has a convex outer surface 43 and a concave inner surface 44 which forms a semi-spherical posterior opening 45. A threaded bore 48 is formed at the apex of shell 40. As is commonly known in the field, outer surface 43 is textured to facilitate securement of the shell in place within the appropriately prepared acetabulum. Shell 40 also includes an outer rim 46. A number of tabs (not shown) protrude from rim 46. As commonly known in the field, the tabs mate with notches 57 in liner 50 to prevent rotational movement of the liner within posterior opening 45. In addition, the tabs mate with notches 17 of head component 10 when shell 40 is secured to instrument 2. As shown in FIG. 4, bearing liner 50 is adapted to be seated within posterior opening 45. Liner 50 has a convex inner surface 52 and a substantially flat outer surface 54. The inner surface 52 of liner 50 is congruent or complimentary to inner surface 44 of shell 40. Liner 50 also has a central cavity 55 formed in the outer surface 54 for receiving a prosthetic femoral ball (not shown). Liner 50 includes a radially projecting side flange 56. Notches 57 are formed along the perimeter of side flange 16 for mating with the tabs protruding from shell 40.

FIG. 3 shows shell 40 connected to instrument 2. As shown in the FIG. 3, head component 10 is juxtaposed between impactor flange 34 and inner surface 44 of shell 40. Extension 36 extends into bore 20 from the liner engaging end of head component 10 such that rounded surface 12 faces away from impactor 30. Threaded distal end 39 protrudes from the shell engaging end of head component 10 and is turned into threaded bore 48 of shell 40. It should be noted that threaded proximal end 37 of extension 36 is journaled freely within the liner engaging end of bore 20. When extension 36 is turned into bore 48, inner surface 44 of shell 40 is seated against rounded surface 12 of head component 10, and flange 34 is drawn against rim 18. Side flange 16 is seated against shell rim 46 to ensure that head component 10 is squarely seated against shell 40. In addition, the tabs protruding from shell rim 46 extend in to notches 17 of side flange 16 to prevent rotational movement of head component 10 within shell 40. With shell 40 securely connected to instrument 2, the shell can be aligned and driven into the acetabulum (not shown). Once shell 40 is seated and secured to the acetabulum, instrument 2 is disconnected from shell 40.

FIG. 4 shows instrument 2 for use in seating bearing liner 50 into shell 40. As shown in FIG. 4, extension 36 extends into bore 20 from the shell engaging end of head component 10 such that flat surface 14 faces away from impactor 30. Threaded proximal end 37 is turned into threaded portion 22 of head component 10 and rounded surface 12 abuts against flange 34. In use, liner 50 is manually positioned at the mouth of posterior opening 45. Flat surface 14 of head component 10 is placed against liner outer surface 54. Annular rim 18 extends into cavity 55 to squarely position head component 10 against liner 50. Impactor 30 can be struck to fit liner 50 into shell 40.

It is understood that the above description does not limit the invention to the details given, but may be modified within the scope of the following claims.

I claim:

1. An instrument for installing an acetabular cup assembly including a hemispherical shell adapted for seating into an acetabulum and having a concave inner surface which defines a posterior opening, and a bearing liner adapted for restrictively seating within said shell posterior opening, said instrument comprising:
   an impactor having a proximal end and a distal end,
   a head part having a first surface adapted for abutment against said shell and a second surface adapted for abutment against said liner, and
   fitting means connected to said impactor distal end for fitting said head part to said impactor in a first position wherein said head part first surface is configured to abut against said shell inner surface, said fitting means for fitting said head part in a second position wherein said head part second surface is positioned to abut against said liner for seating said liner into said shell posterior opening
   wherein said fitting means includes an extension part extending from said impactor distal end, said head part has a bore defined between said head part first surface and said head part second surface and adapted for receiving said extension part therein from one direction when said head part is connected to said impactor in said first position and for receiving said extension part therein from the opposite direction when said head .part is connected to said impactor in said second position.

2. The instrument of claim 1 wherein said extension part includes connecting means protruding from said head part first surface when said head part is fitted to said impactor in said first position for connecting said shell to said instrument, whereby said head part is secured between said impactor distal end and said shell inner surface.

3. The instrument of claim 2 wherein,
   said head part includes a peripheral flange for seating against a rim of the shell to ensure proper seating of said head part first surface against said shell inner surface.

4. The instrument of claim 2 wherein,
   said connecting means includes a threaded portion formed in said extension part for connectively engaging a threaded bore in the shell and said head part may be secured to said impactor in said first position when said shell is connected to said instrument.

5. The instrument of claim 1 wherein said extension part includes connecting means for connectively engaging said head part when said head part is connected to said impactor in said second position.

6. The instrument of claim 5 wherein said head part bore has a threaded portion,
   said connecting means includes a threaded portion formed in said extension part and connectively engaged within said head part bore threaded portion when said head part is connected to said impactor in said second position.

* * * * *